United States Patent
De Smet

(10) Patent No.: US 8,988,071 B2
(45) Date of Patent: Mar. 24, 2015

(54) NONDESTRUCTIVE INSPECTION OF A STRUCTURE IN AN AIRCRAFT

(75) Inventor: Marie-Anne De Smet, Monbrun (FR)

(73) Assignee: AIRBUS Operations S.A.S., Toulouse (FR)

( * ) Notice: Subject to any disclaimer, the term of this patent is extended or adjusted under 35 U.S.C. 154(b) by 728 days.

(21) Appl. No.: 13/224,586

(22) Filed: Sep. 2, 2011

(65) Prior Publication Data

US 2012/0074932 A1 Mar. 29, 2012

(30) Foreign Application Priority Data

Sep. 23, 2010 (FR) ...................................... 10 57643

(51) Int. Cl.
*G01N 27/82* (2006.01)
*G01N 27/90* (2006.01)
(52) U.S. Cl.
CPC .......... *G01N 27/9046* (2013.01); *G01N 27/904* (2013.01)
USPC .............................. 324/240; 702/58; 702/183
(58) Field of Classification Search
USPC ............. 324/240, 219, 239, 257; 702/58, 183
See application file for complete search history.

(56) References Cited

U.S. PATENT DOCUMENTS

| | | | | | |
|---|---|---|---|---|---|
| 5,623,204 | A | * | 4/1997 | Wilkerson ..................... | 324/228 |
| 7,250,757 | B1 | | 7/2007 | Tiernan | |
| 2002/0158626 | A1 | * | 10/2002 | Shay et al. ............... | 324/207.16 |
| 2002/0163333 | A1 | * | 11/2002 | Schlicker et al. ............. | 324/242 |
| 2002/0190724 | A1 | * | 12/2002 | Plotnikov et al. ............. | 324/529 |
| 2004/0004475 | A1 | * | 1/2004 | Goldfine et al. .............. | 324/242 |
| 2004/0124834 | A1 | * | 7/2004 | Goldfine et al. .............. | 324/243 |
| 2005/0264284 | A1 | * | 12/2005 | Wang et al. .................... | 324/240 |
| 2006/0186880 | A1 | | 8/2006 | Schlicker et al. | |
| 2007/0007955 | A1 | * | 1/2007 | Goldfine et al. .............. | 324/240 |
| 2009/0091318 | A1 | * | 4/2009 | Lepage et al. ................ | 324/242 |
| 2009/0115410 | A1 | * | 5/2009 | McKnight et al. ............ | 324/240 |
| 2009/0230952 | A1 | * | 9/2009 | Endo et al. .................... | 324/238 |
| 2010/0079157 | A1 | * | 4/2010 | Wincheski et al. ........... | 324/699 |

FOREIGN PATENT DOCUMENTS

| | | | |
|---|---|---|---|
| GB | 2 401 947 A | | 11/2004 |
| SU | 700830 | * | 6/1978 |

OTHER PUBLICATIONS

European Search Report issued Dec. 7, 2011, in Patent Application No. EP 11 18 2121 (with Translation of Category of Cited Documents).
Theodoros Theodoulidis, et al., "Interaction of an Eddy-Current Coil With a Right-Angled Conductive Wedge", IEEE Transactions on Magnetics, vol. 46, No. 4, XP011297661, Apr. 1, 2010, pp. 1034-1042.

* cited by examiner

*Primary Examiner* — Huy Q Phan
*Assistant Examiner* — Giovanni Astacio-Oquendo
(74) *Attorney, Agent, or Firm* — Oblon, McClelland, Maier & Neustadtm L.L.P.

(57) ABSTRACT

The invention relates to a non-destructive inspection method using eddy currents for detecting flaws in a metal structure (3) by means of an array (5) of coils attached to a surface (31) of said structure (3) comprising activation of the coils, measurement of the electrical signals representative of the eddy currents, and evaluation over time of a variation in the electrical signal of each of the coils (511-536) by taking as a reference an edge effect corresponding to a specific electrical signal emanating from at least one coil installed at the edge of the surface, the level of said variation being indicative of the presence of the flaws in the structure.

13 Claims, 7 Drawing Sheets

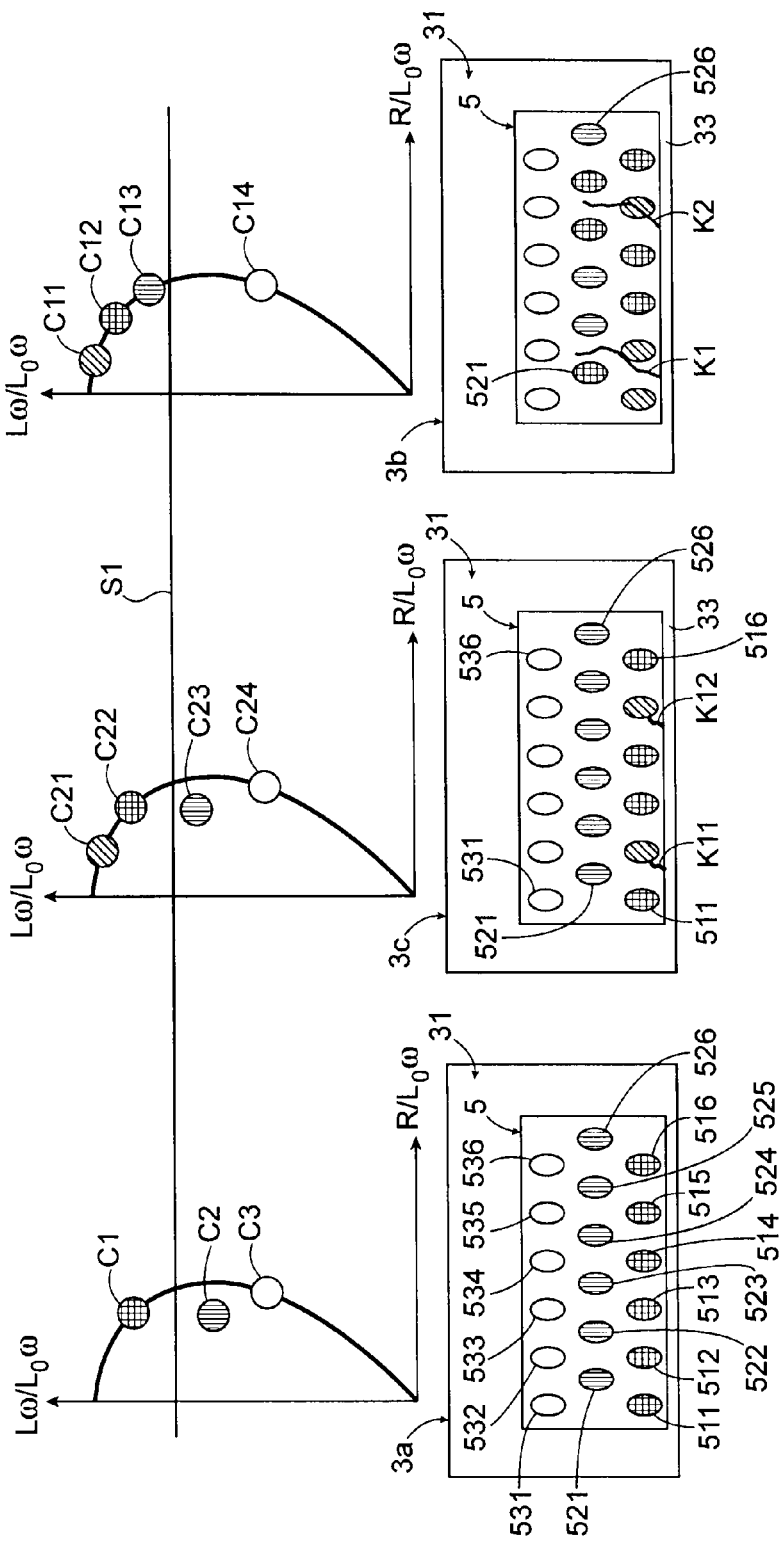

NONDESTRUCTIVE INSPECTION OF A STRUCTURE IN AN AIRCRAFT

TECHNICAL FIELD

The present invention relates to the field of nondestructive inspection techniques for detecting flaws in metal structures, and more particularly for detecting cracks in areas of the structure of an aircraft that are inaccessible or accessible only with difficulty.

PRIOR STATE OF THE ART

The structures or mechanical parts of aircrafts are subject to regular inspections for detecting in particular the possible presence of cracks in order to proceed, if necessary, with appropriate repairs.

Already known through patent application EP2037261 is a nondestructive inspection system comprising a probe consisting of a plurality of fixed coils attached to the surface to be inspected. Subsets of these coils are sequentially fed and connected in series to simulate a continuous sweep of the surface to be inspected by a probe. The initialization of the coils is performed in air before their installation onto the surface and the signals emanating from the subsets of coils are compared with one another to detect surface cracks in the structure.

However, this system can also trigger alerts which do not necessarily correspond to cracks. Indeed, electromagnetic interference and/or temperature changes and/or changes in the mechanical properties of the structure (for example, hardening of the material) can disturb the circulation of eddy currents and bring about a variation in impedance at the coils.

The object of the present invention is to propose a nondestructive inspection method using eddy currents to detect possible flaws in a metal structure that corrects the aforementioned disadvantages, in particular by making it possible to detect cracks without being disturbed by external factors or by a natural change in the structure.

DESCRIPTION OF THE INVENTION

The invention has as its object a nondestructive inspection method using eddy currents for detecting flaws in a metal structure by means of an array of coils attached to a surface of said structure, comprising activation of the coils, and measurement of electrical signals representative of the eddy currents, said method also comprising evaluation over time of variation in the electrical signal of each of the coils, using as a reference an edge effect corresponding to a specific electrical signal emanating from at least one coil installed at the edge of the surface, the level of said variation being indicative of the presence of flaws in the structure.

Thus, the method according to the invention makes it possible to have automatic, accurate and reliable detection of flaws in areas where there is no access while still avoiding false alarms.

Advantageously, the method includes a step for comparing the specific electrical signals of the coils installed at the edge of the surface to one another.

This allows cross-comparison with the preceding results in order to be more sure of not having a false diagnosis.

According to an advantageous feature of the present invention, the method also comprises the following steps:
determining a spatial mapping by establishing a correspondence between the levels of the electrical signals of the coils compared with the edge effect in the impedance plane and the spatial distribution of said coils on said surface, and
displaying said spatial mapping.

This makes it possible to directly locate the position of any coil indicating the presence of a flaw.

Advantageously, the method comprises the following steps:
assembling each of the coils of said array to the surface of said structure using a flexible material having adhesion, covering the array of coils using said flexible material, and maintaining the array of coils in contact on said surface by means of said flexible material.

This allows perfect fitting of the coils over any geometric shape of the surface, better contact and better protection of the array.

According to one aspect of the invention, the method comprises an analysis of the electrical signals emanating from the coils with respect to detection thresholds determined according to the positions of said coils on the surface.

These crack detection thresholds make it possible to quickly and effectively determine whether the electrical signal levels of the coils are acceptable or not for the structure.

Advantageously, the method comprises a calibration of said coil array at predetermined intervals in time to analyze the change on the surface of said structure.

This makes it possible to effectively diagnose at any time the operational status of each coil.

Advantageously, the method comprises exclusion of the electrical signal of any coil having an anomaly.

This allows detection to be carried out even if one or more coil(s) is (are) defective.

According to another aspect of the invention, the method comprises the following steps:
determining the phases of said electrical signals emanating from the coils while taking the edge effect as a reference, and
analyzing the phase shifts of said electrical signals compared to a reference phase corresponding to surface eddy currents.

This makes it possible to detect deep-lying flaws in addition to surface cracks.

The invention also relates to a nondestructive inspection device using eddy currents for detecting flaws in a metal structure by means of an array of coils attached to a surface of said structure, comprising activation means for activating the coils, measurement means for measuring electrical signals representative of the eddy currents, and data processing means for evaluating over time a variation in the electrical signal of each of the coils by using as a reference an edge effect corresponding to a specific electrical signal emanating from at least one coil installed at the edge of the surface, the level of said variation being indicative of the presence of flaws in the structure.

The invention also relates to an aircraft comprising a metal structure and a device for inspecting the structure implementing the method according to any one of the above features.

BRIEF DESCRIPTION OF DRAWINGS

Other features and advantages of the invention will appear upon reading the preferred embodiments of the invention made with reference to the appended figures in which.

FIGS. 4A-4C shows a detection threshold in the impedance plane that can be used to diagnose the presence of flaws in the structure of the aircraft;

DETAILED DESCRIPTION OF PARTICULAR EMBODIMENTS

The invention relates to the detection by eddy currents of flaws in a metal structure using an on-board array of coils. The basic principle of the invention is to analyze the signals emanating from the coils by comparison with an edge effect.

Figure 1A:
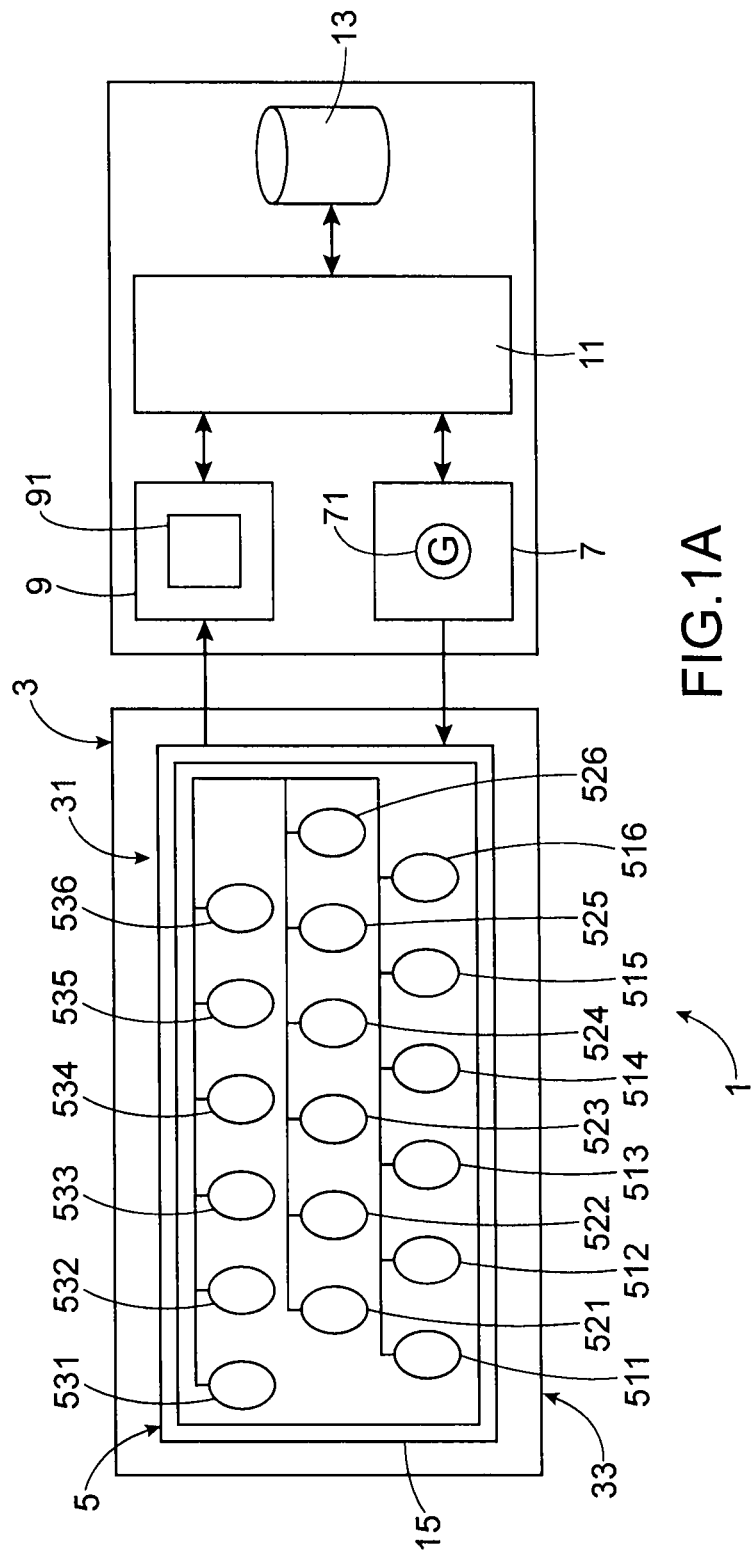
FIGS. 1A and 1B illustrate schematically a device that can be used to carry out the nondestructive inspection method using eddy currents to detect flaws in a metal structure of an aircraft, according to the invention.
Figure 1B:
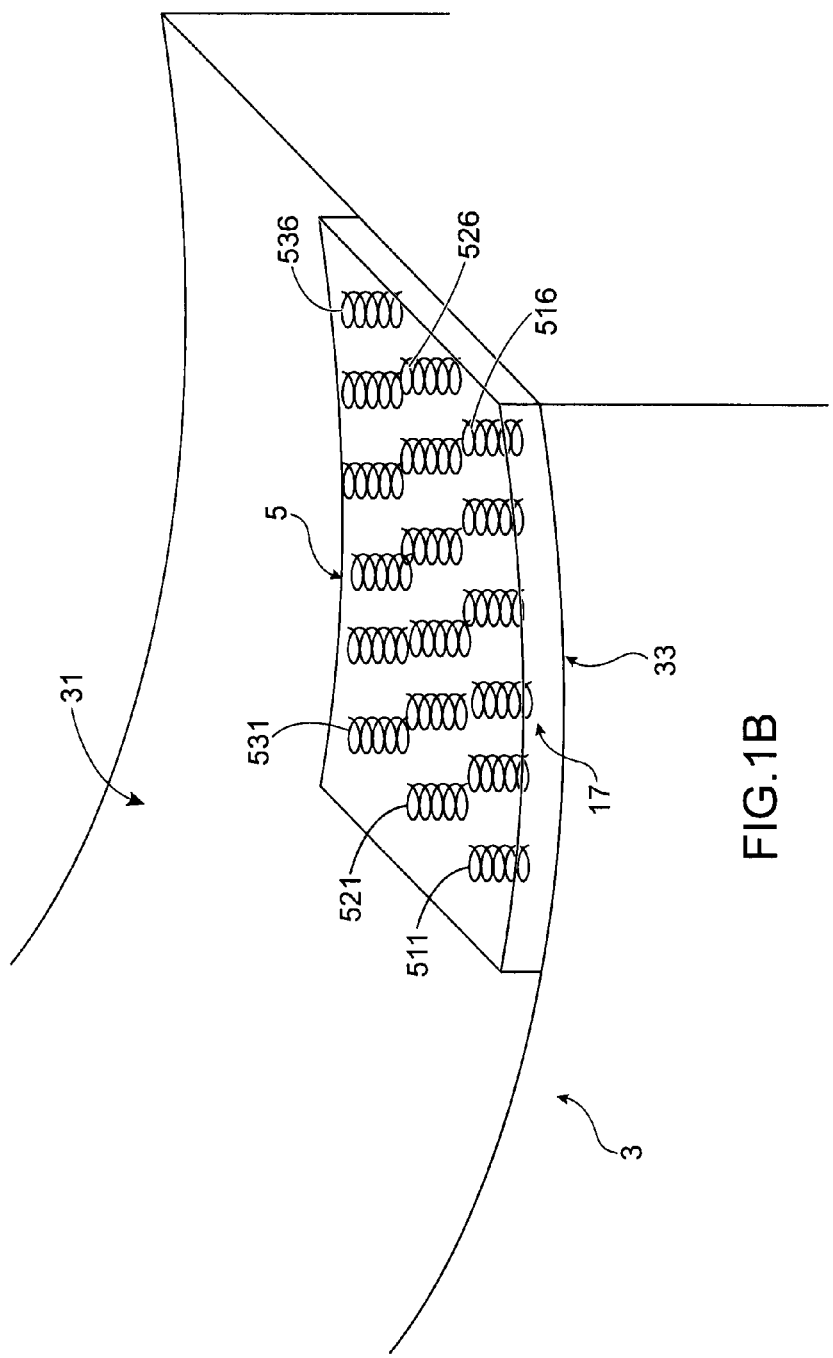

FIGS. 1A and 1B illustrate schematically a device that can be used to carry out the non-destructive inspection method using eddy currents for detecting flaws in a metal structure of an aircraft, according to the invention.

The device 1 comprises an array 5 of coils, activation means 7 for activating the coils, measurement means 9 for measuring the electrical signals representative of eddy currents, calculation or data processing means 11 for processing and analyzing the electrical signals, and memory means 13 for recording data or code instructions of a computer program.

The coil array 5 consists of a plurality of coils 511-536 connected in parallel to be treated individually as a plurality of eddy-current sensors. It will be noted that the coils 511-536 can be of planar or volumetric form depending on the thickness, the bulk and other factors of the structure to be inspected. By way of example, each coil can have a diameter of about 0.5 mm to 1 mm, and a height of about 1 mm to 5 mm. Thus the diameter of the coils 511-536 can be matched to the smallest flaw to be detected, usually of the order of 1 mm, and even allows the detection of cracks smaller than 1 mm. In addition, depending on the height of the coils 511-536, the device 1 can detect flaws at several depth levels within the structure 3. This is particularly advantageous in assemblies which have no direct access to the skin of the structure.

The coil array 5 is arranged so as to cover the entire surface 31 of the structure 3 to be inspected. It will be noted that the coil array 5 comprises a frame 15 or electromagnetic screen to isolate it from its environment while allowing each coil a fairly extensive individual detection field to avoid the existence of dead zones between the coils 511-536. Thus, the coil array 5 can continuously diagnose the entire surface bounded by the frame 15.

Advantageously, the coil array 5 is held on the surface to be inspected by a flexible material 17 possessing adhesion, of the gap-filling mastic type hence not aggressive to the structure to be inspected, and resistant to aggressive liquids such as kerosene for example. The flexible material 17 is used to assemble each of the coils to the surface 31 of the structure. This flexible material 17 makes it possible to fit and to hold the coil array 5 in contact on a surface 31 of any geometric shape (for example plane, concave or convex). Advantageously, the flexible material 17 is used to cover the coil array 5 in order to fix and protect it against any aggressive product.

After attachment of the array 5 on the surface 31 of the structure of the coils, the coils are activated and their electrical signals are measured.

Indeed, the activation means 7 comprise a variable current generator 71, of the sinusoidal type for example, for individually activating the coils 511-536. The generator 71 feeds the coils 511-536 with an excitation frequency that can be selected depending on parameters connected with the material of the structure 3 such as for example its electrical conductivity, its magnetic permeability, as well as the geometric shape and the thickness of the structure 3, etc.

The measurement means 9 comprise means of amplification, of filtering, and detectors of the active and reactive components of the signals (not shown), as well as display means 91 to for example display the amplitude and the phase of the signals or even the active and reactive components in the complex plane. The measurement means 9 can possibly include automatic balancing means.

In conformity with the invention, the method comprises an evaluation over time of a variation in the electrical signal of each of the coils 511-536 using as a reference an edge effect corresponding to a specific electrical signal emanating from at least one coil 511-516 installed on the edge 33 of the surface 31, the level of said variation being indicative of the presence of the flaws in the structure.

Indeed, the processing means 11 are configured for determining or evaluating this variation over time of the electrical signal. It will be noted that the electrical signal of each coil can be represented in the complex plane, or more precisely the impedance plane (see FIGS. 2 through 4C) such that the level of variation of the electrical signal is indicative of the presence or absence of flaws in the structure 3. Thus, possible flaws in the structure 3 can be detected by analyzing for example the change over time of the amplitude of the signal or the impedance of each coil compared with the edge effect.

It will be noted that the edge effect is a relative reference which changes with the changing and the aging of the structure 3, and consequently a signal determined by comparison with this reference remains invariant with respect to external factors. Indeed, if a general change occurs due to the aging or hardening of the material, to the presence of an external electromagnetic field, to overheating of the structure or to any other extrinsic effect, the response of the material changes in consequence. But this change affects simultaneously and in essentially the same manner all the signals of the coils 511-536 and consequently, by determining the signals by comparison with the edge effect, all these material aging or extrinsic factors phenomena will have no impact on the detection of cracks or flaws and false alarms are thus avoided.

In addition, using the edge effect as a reference, the initialization of the array 5 can be carried out directly on the structure 3 and it is no longer necessary to "zero" the coils in air. Thus, the processing means 11 can be configured to calibrate (initialize or reinitialize) the coil network 5 at set intervals in time (for example, before each inspection) while having the latter attached on the surface 31 of the structure 3. The recording of these calibrations makes it possible to analyze the change on the surface of the structure 3.

Calibration makes it possible to analyze the conformity of the signals of the coils 511-536 while still having the array 5 permanently installed on the structure 3, thus allowing comparison of the signals at different moments in time and consequently, to diagnose the operational status of each coil effectively and reliably. In particular, this makes it possible to avoid the risk of incorrect interpretation of the signal due to a bad contact. The processing means 11 can be configured to exclude the signal of any coil having an anomaly, consequently allowing the use of the inspection device 1 even if one or more coils are defective.

According to a particular embodiment, the processing means 11 can be configured to subdivide or define subsets of coils among the coils 511-536 of the array 5 such that each subset comprises at least one edge coil among the coils 511-516 installed on the edge of the surface 31. Each subset of coils can for example correspond to an alignment of coils substantially perpendicular to the surface.

By way of example, the array 5 can be subdivided into the following subsets: (511, 521, 531), (512, 522, 532), . . . , (516, 526, 536). The first edge coil 511 of the first subset (511, 521, 531) can be used as a reference for determining the signals or impedances of the coils 511, 521, 531 belonging to this first subset. The second edge coil 512 can be used as a reference for the second subset, and so on. Indeed, for each subset, the processing means 11 determine the electrical signal of each of its coils by taking as a reference the edge effect corresponding to the specific signal emanating from the edge coil belonging to said subset. This allows the processing means 11 to compare for each subset the change in the electrical signal of each of its coils at different moments in time.

It will be noted that each of the subsets of coils can comprise two edge coils or more by grouping them for example two-dimensionally. In addition, the subsets can be selected to be non-independent by having coils in common.

Furthermore, according to a first variation, the subsets of coils can be simultaneously activated by the activation means 7. According to a second variation, they can be activated sequentially (one subset to each sequence) to simulate a mechanical sweep of the surface 31 to be inspected.

Figure 2:
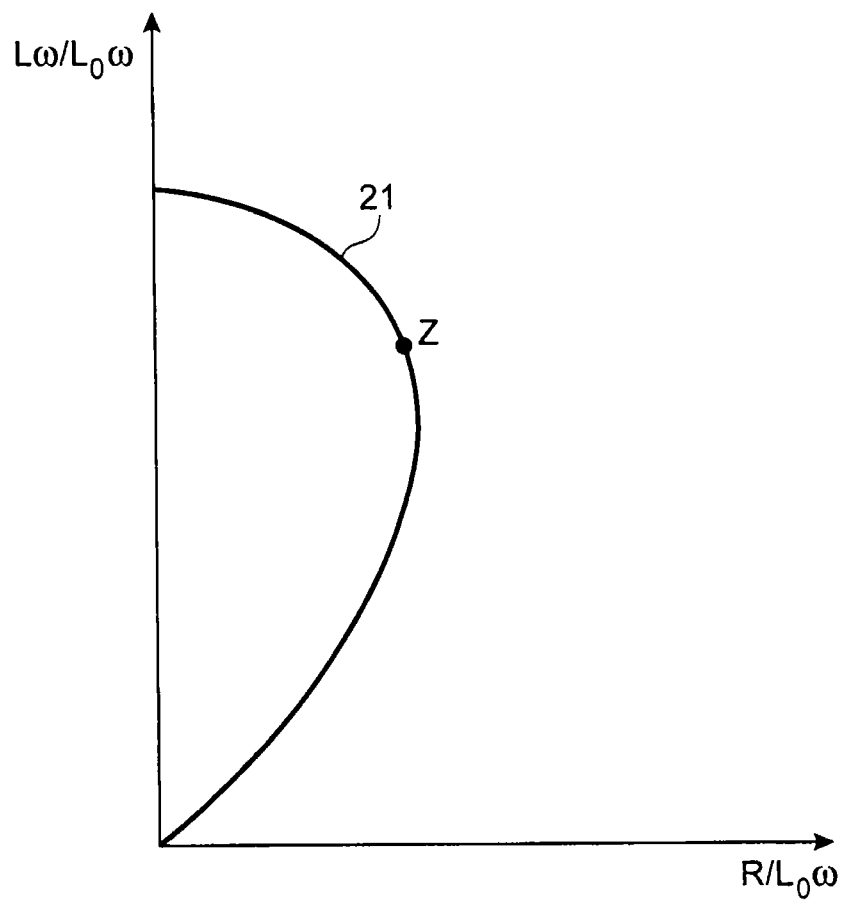
FIG. 2 shows an example of a conventional impedance diagram of a coil of the device of FIG. 1, in the impedance plane.

FIG. 2 shows an example of a conventional impedance diagram of a coil in the impedance plane. Each point on the curve 21 represents a normalized impedance Z defined by a normalized active component $R/L_0 \omega$ and a normalized reactive component $L\omega/L_0 \omega$ (R being the resistance of the coil, L being the inductance of the coil, $L_0$ being the inductance of the coil before installation and $\omega$ being the pulse rate).

Figure 3A:
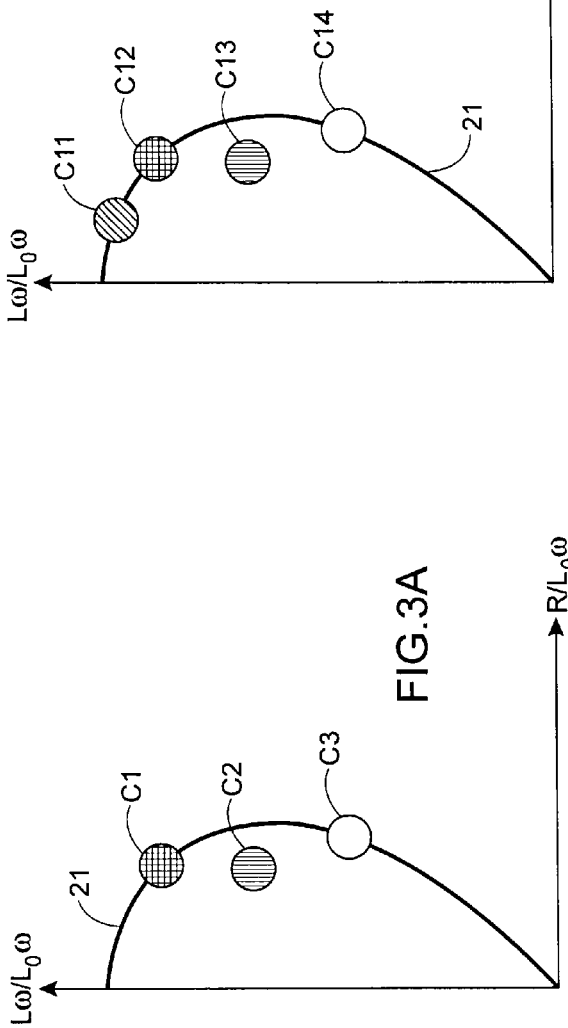
FIGS. 3A and 3B show the distribution of the normalized impedances emanating from the coils as a function of their position on the structure of the aircraft.

FIG. 3A shows the distribution of the normalized impedances Z emanating from the coils as a function of their position on an initial or reference structure 3a having no flaws. Each small circle on the curve 21 represents the impedance of a coil which depends in particular on the distance between the coil and the edge 33 of the structure 3. The coils 511-516 installed at the edge 33 of the surface 3 have the highest impedances and those 531-536 which are the farthest from the edge 33 have the lowest impedances.

More particularly, according to this example, the small circles C1, C2, and C3 represent, starting from the edge 33, the coils 511-516 in the first row, the coils 521-526 in the second row, and the coils 531-536 in the third row respectively. The edge effect acts on each coil according to its distance from the edge 33. In particular, the edge 33 can be considered an infinite cross-section crack which prevents the eddy currents from circulating. Conversely, a crack can be considered an edge and consequently, a coil in the vicinity of a crack has an impedance equivalent, or rather comparable, to that of a coil installed at the edge.

Thus, the detection and the monitoring of the propagation of a crack can be carried out by measurement and comparison of the electrical signal of each of the coils 511-536, against those which are on the edge, 511-516. The propagation of a crack can be read by the appearance of a signal comparable to that of an edge coil and therefore can be classified in a category of "crack signal."

Figure 3B:
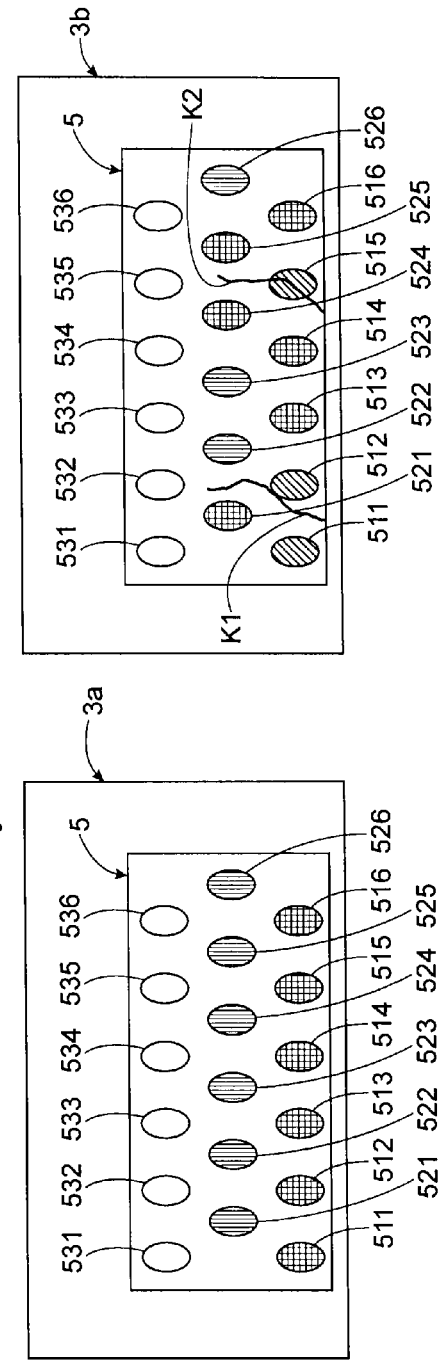

FIG. 3B shows a distribution of the signals emanating from the coils as a function of their position on a structure 3b having flaws.

By way of example, the edge coils 511, 512 and 515 which have cracks K1 and K2 in their vicinity, have a higher impedance (represented by the small circle C11) than that (represented by the small circle C12) of the coils 513 and 514 which do not have cracks in their immediate vicinity. Likewise, the coils in the second row, 521, 524 and 525, have a higher impedance (represented by the small circle C12) than that (represented by the small circle C13) of the coils 522 and 523. In addition, the impedance of the coils 531-536 of the third row is represented by the small circle C14.

As previously stated, a crack or fissure prevents the eddy currents from circulating and consequently the impedance of a coil in the immediate vicinity of the crack will increase. Moreover, the effect of a crack combines with the edge effect and consequently the signals emanating from two coils equidistant from the edge for example can only be differentiated by the existence of a crack in the immediate vicinity of one or the other of the two coils.

Practically, the variation with time of the electrical signals emanating from the coils can be analyzed by comparing these signals to detection thresholds which allow direct diagnosis of flaws or cracks in the structure 3.

Indeed, FIGS. 4A-4C show a detection threshold S1 in the impedance plane which can be used for diagnosing the presence of the flaws in the structure 3. According to this example, the threshold S1 is used for the group of coils 521-526 installed in the second row.

More generally, the processing means 11 are advantageously configured for analyzing the electrical signals emanating from the coils with respect to detection thresholds determined according to the positions of the coils on the surface 31. In this way, a detection threshold can correspond to each coil or to each group of coils equidistant from the edge 33. In other words, the detection thresholds depend on the spatial distribution of the coils and in particular on their distance from the edge 33 of the surface 31. For example, the edge coils are processed with a different threshold because at the outset they have higher impedance levels due to the edge effect.

Generally, the detection thresholds make it possible to determine whether the levels of the electrical signals of the coils are acceptable or not for the structure 3.

FIG. 4A illustrates the case of a structure 3a with no flaws and represents the detection threshold S1 corresponding to the coils 521-526 installed in the second row. According to this example, the signals (represented by the small circle C2) emanating from these coils are of course below the corresponding detection threshold S1.

FIG. 4B illustrates the case where the structure 3c has a few small cracks K11, K12 considered as acceptable because the signals (represented by the small circle C23) emanating from the coils 521-526 are always below the corresponding detection threshold S1 even though they are close to that threshold.

FIG. 4C, on the other hand, illustrates the case where the cracks K1, K2 in the structure 3b are larger with signals (represented by the small circle C13), emanating from the coils 521-526, which exceed the corresponding detection threshold S1. In this latter case, an alert is issued.

Moreover, the processing means 11 are configured to analyze the spatial distribution of the coils which have electrical signals the levels whereof exceed the detection thresholds.

This analysis makes it possible to check whether these levels exceed another acceptability threshold expressed as crack length in order to detect the length of fissures or cracks not to be exceeded.

Further, the processing means 11 are also configured to compare to one another the specific signals of the coils 511-516 installed at the edge 33 of the surface 31. This analysis in parallel of all the coils 511-516 which are aligned at the edge of the structure 3 makes it possible to cross-compare the previous results in order to be even more sure of not having a false diagnosis. Indeed, this makes it possible to accurately check whether the alert or the flaw detection by analysis of the variation of the electrical signals of the coils truly corresponds to a crack or a flaw and not to a local change in the properties of the material due for example to a thermal field, an electromagnetic field, a detachment of the coils from the surface or any other external effect. In particular, if the amplitude or impedance levels of a large part of the edge coils 511-516 indicate the presence of a flaw, it can be deduced that the cause is likely something other than a crack in the structure 3. Indeed, an edge crack is generally detected only by one, possibly two edge coils and consequently, a flaw detected by a large number of edge coils can be considered suspect knowing that it is extremely improbable to have as many cracks as there are coils.

Further, the processing means 11 are advantageously configured for determining a spatial mapping according to a c-scan type reporting mode giving the respective positions of the coils detecting the flaws or cracks. This spatial mapping can be carried out by establishing a correspondence between the levels of the electrical signals of the coils compared to the edge effect in the impedance plane and the spatial distribution of these coils on the surface 31 of the structure 3. The display means 91 can then directly display this spatial mapping, which makes it possible to determine the positions of the cracks or flaws in the structure. By way of example, the coils 511-536 represented in FIGS. 4A-4C and the corresponding signals (C1, C2, C3, C21; C22, C23, C24; C11, C12, C13, and C14) are cross-hatched the same way. It will be noted that in order to facilitate the diagnosis, the coils can be displayed on display means 91 in different colors corresponding to different signal levels.

Figure 5:
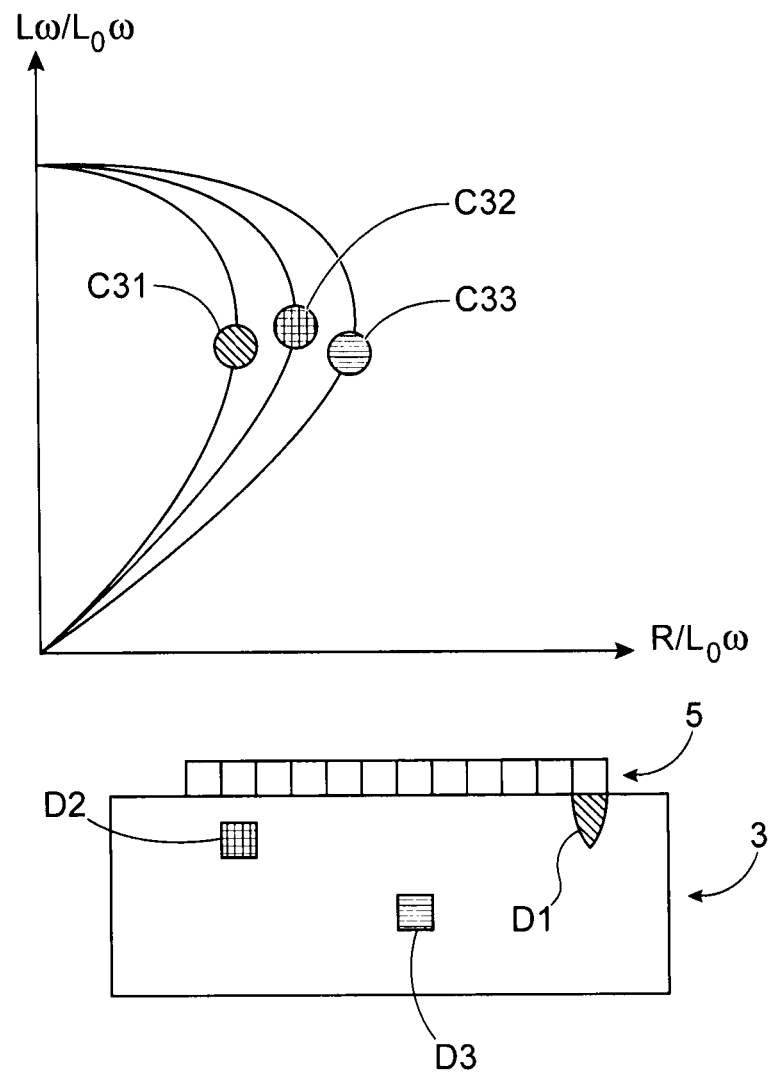
FIG. 5 shows an example of detection of the deep-lying flaws in the structure of the aircraft.

It will be noted that in the case where the array comprises volumetric coils (for example, coils the height whereof is of the order of 5 mm), the active and reactive components of the impedance in the complex plane can be used to detect deep-lying flaws, as illustrated in FIG. 5.

Thus, the processing means 11 are configured to determine the phases of the signals which were already defined with respect to the edge effect. The processing means 11 analyze the phase shifts of the signals with respect to a reference phase corresponding to surface eddy currents. Indeed, the surface eddy currents have a certain phase which can be considered a reference phase, and the deeper one goes into the structure 3 the more the phase will be shifted with respect to the reference phase. In particular, a standard depth is defined by a phase shift of 57° with respect to the surface eddy currents and hence an angle change can be used to diagnose the position of a flaw within the thickness of the structure 3. Thus, the phase shift of the signals gives an indication of the depth of a crack or of the level where a flaw buried in the structure 3 is located. This is particularly advantageous in the case of a structure made up of a stack of several layers for diagnosing cracks that could for instance start in an intermediate layer.

The example of FIG. 5 shows a section of the structure 3 having a first surface flaw D1, a second deep-lying flaw D2 and a third flaw D3 at even greater depth. The small circles C31, C32, and C33 show the signals emanating from the coils detecting the flaws D1, D2, and D3 respectively. The angle variations of the signals C31, C32, and C33 indicate the depth of the flaws within the structure 3.

Further, it will be noted that the inspection device 1 according to the invention can be integrated into an aircraft health monitoring system. The diagnosis carried out by the inspection device can be checked at rest or even continuously during operation of the structures of the aircraft. This makes it possible to enrich the monitoring of the aircraft's health.

Figure 6:
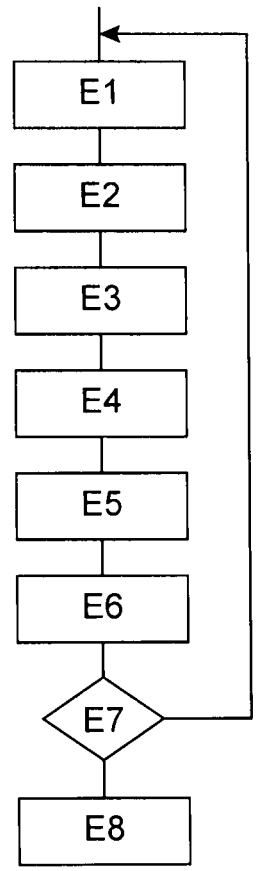
FIG. 6 shows a flowchart illustrating the different steps in the installation of the coil array on the structure of the aircraft according to the invention.

FIG. 6 shows a flowchart illustrating the different steps in the installation of the coil array 5 on a structure 3 of the aircraft according to a particular embodiment of the invention.

At Step E1 a molding tool is installed on the area of the surface 31 that is to be covered.

At Step E2, an array 5 consisting of small coils associated in parallel is mounted in the molding tool and in contact with the surface 31 to be inspected of the structure 3.

At Step E3, the flexible filler material 17 (mastic) is poured into the molding tool and over the coil array 5 in order to cover the coils while also holding them in contact with the surface 21. After polymerization of the mastic, the latter allows adhesion of the coil array 5 to the metal skin (surface) of the structure 3.

At Step E4, the coils are individually activated by a variable electric generator.

At Step E5, the electrical signals emanating from the coils are sampled by the measurement means 9.

At Step E6, the processing means 11 determine the distribution in the impedance plane of the signals emanating from the coils, using the edge effect as a reference.

At Step E7, the processing means 11 carry out an electronic diagnostic or automatic calibration of the coils by analyzing the conformity of an electronic threshold of each of the coils. More particularly, the signals emanating from the coils are analyzed with respect to the geometry of the structure. If the spacing of the signals in the impedance plane is homogeneous (in other words, if the coils set at equal distances from the edge 33 have the same impedance levels), then it can be inferred that the coils are operating properly. If, however, the spacing of the signals is not homogeneous, then it can be inferred that there exists at least one coil in the array which was damaged during installation. In this latter case, the array 5 may possibly be removed to be repaired or replaced and the foregoing installation steps are repeated. It will be noted that this analysis can be supplemented by a diagnostic based on comparison of the electronic thresholds over time for a possible detection of abnormal variation of the coil signal due to an incipient break in a cable or in an electrical connection. If the coil shows this type of anomaly, its signal will be automatically excluded.

At Step E8, the processing means 11 record in the memory means 13 reference data corresponding to a signature of the individual signals of the coils making up the array 5 for future comparisons and diagnosis of proper operation over time.

Figure 7:
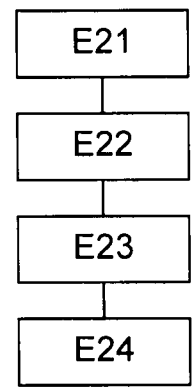
FIG. 7 shows a flowchart illustrating the different steps of the method for detecting flaws in the structure of the aircraft according to a particular embodiment of the invention.

FIG. 7 shows a flowchart illustrating the different steps in the flaw detection method according to a particular embodiment of the invention.

At Step E21 the coils 511-536 are individually activated by the electric generator. The coils can be activated simultaneously or in a mode providing a virtual sweep of the surface 31 by sequences of a predetermined number of coils comprising at least one edge coil in each sequence.

At Step E22, the processing means 11 record in the memory means 13 initial data corresponding to initial signals of the coils.

At Step E23, the processing means compare the initial data to the reference data to determine the variation over time of the electrical signal of each of the coils, using the edge effect as a reference. If for a given coil the variation exceeds a predetermined value, then it can be inferred that the coil is detecting a flaw. This can be confirmed when there are two or more neighboring coils which also indicate variations greater than predetermined values.

At Step E24, the processing means 11 compare with one another the signals of the coils installed at the edge 33 of the surface 31. This makes it possible to cross-compare the previous results to check that the detection truly corresponds to a crack or a flaw and is not a false alarm.

Further, it will be noted that the memory means 13 can include a computer program comprising code instructions designed to implement the method according to the invention as described above when it is executed by the processing means 11.

The invention claimed is:

1. A nondestructive inspection method using eddy currents for detecting flaws in a metal structure by an array of coils attached to a surface of said structure, comprising:
   activating the coils;
   measuring electrical signals of the coils representative of the eddy currents;
   comparing the electrical signal of each of the coils with a specific electrical signal emanating from at least one coil installed at an edge of the surface; and
   evaluating over time the comparing of the electrical signal of each of the coils, to detect a variation in the electrical signal of each of the coils with respect to a reference that is an edge effect corresponding to the specific electrical signal emanating from at least one coil installed at the edge of the surface, a level of said variation being indicative of a presence of one or more of the flaws in the structure.

2. The inspection method according to claim 1, further comprising comparing to one another the specific electrical signals of the coils installed at the edge of the surface.

3. The inspection method according to claim 1, further comprising:
   determining a spatial mapping by establishing a correspondence between the levels of the electrical signals of the coils compared to the edge effect in an impedance plane and a spatial distribution of said coils on said surface, and
   displaying said spatial mapping.

4. The inspection method according to claim 1, further comprising:
   assembling each of the coils of said array of coils onto the surface of said structure by a flexible material possessing adhesion,
   covering the array of coils by the flexible material, and
   holding the array in contact on said surface by said flexible material.

5. The inspection method according to claim 1, further comprising analyzing the electrical signals emanating from the coils by a comparison with detection thresholds determined as a function of positions of said coils on the surface.

6. The inspection method according to claim 1, further comprising calibrating said array of coils at predetermined intervals in time to analyze a change on the surface of said structure.

7. The inspection method according to claim 1, further comprising excluding the electrical signal of any coil showing an anomaly.

8. The inspection method according to claim 1, further comprising:
   determining phases of said electrical signals emanating from the coils, taking the edge effect as a reference, and
   analyzing phase shifts of said electrical signals with respect to a reference phase corresponding to surface eddy currents.

9. An aircraft comprising a metal structure and an inspection device for or the structure implementing the method according to claim 1.

10. The inspection method according to claim 1, further comprising calibrating said array of coils while the array of coils is attached on the surface of said structure.

11. The inspection method according to claim 1, wherein said coils are electrically connected in parallel.

12. A non-destructive inspection device using eddy currents for detecting flaws in a metal structure by an array of coils attached on a surface of said structure, comprising:
   activation means for activating the coils; and
   measurement means for measuring electrical signals of the coils representative of the eddy currents,
   wherein the non-destructive inspection device is configured to compare the electrical signal of each of the coils with a specific electrical signal emanating from at least one coil installed at an edge of the surface, and also configured to evaluate over time the comparing of the electrical signal of each of the coils, to detect a variation of the electrical signal of each of the coils with respect to a reference that is an edge effect corresponding to the specific electrical signal emanating from at least one coil installed at the edge of the surface, a level of said variation being indicative of a presence of one or more of the flaws in the structure.

13. A non-destructive inspection device using eddy currents for detecting flaws in a metal structure an array of coils attached on a surface of said structure, comprising:
   circuitry configured to:
      activate the coils,
      measure electrical signals of the coils representative of the eddy currents;
      compare the electrical signal of each of the coils with a specific electrical signal emanating from at least one coil installed at an edge of the surface; and
      evaluate over time the comparing of the electrical signal of each of the coils, to detect a variation of the electrical signal of each of the coils with respect to a reference that is an edge effect corresponding to the specific electrical signal emanating from at least one coil installed at the edge of the surface, a level of said variation being indicative of a presence of one or more of the flaws in the structure.

* * * * *